US00PP18189P2

(12) United States Plant Patent
Houbraken

(10) Patent No.: US PP18,189 P2
(45) Date of Patent: Nov. 6, 2007

(54) ***OSTEOSPERMUM* PLANT NAMED 'OSJASECLIPUR'**

(50) Latin Name: *Osteospermum ecklonis*
Varietal Denomination: Osjaseclipur

(75) Inventor: Anna M. W. P. Houbraken, Enkhuizen (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/430,147

(22) Filed: May 8, 2006

(51) Int. Cl.
*A01H 5/00* (2006.01)

(52) U.S. Cl. ..... Plt./360

(58) Field of Classification Search ..... Plt./360
See application file for complete search history.

(56) References Cited

PUBLICATIONS

UPOV ROM GTITM Computer Database GTI Jouve Retrieval Software 2006/04, Citation(s) for 'Osjaceclipur'.*

* cited by examiner

*Primary Examiner*—Wendy C. Haas
(74) *Attorney, Agent, or Firm*—Bruce Vrana

(57) ABSTRACT

A new *Osteospermum* plant particularly distinguished by its compact round plant habit, early flowering with light purple colored, spatulate shaped, ray florets.

1 Drawing Sheet

Latin name of the genus and species of the plant claimed: *Osteospermum ecklonis.*
Varietal denomination: 'Osjaseclipur'.

BACKGROUND OF THE NEW PLANT

The present invention relates to a new and distinct cultivar of *Osteospermum* plant, botanically known as *Osteospermum ecklonis.*

The new *Osteospermum* is propagated by cuttings resulting from an open pollinated population from a proprietary *Osteospermum ecklonis* seedling selection as the female, or seed, parent identified as breeder's code 'C0254-3' (unpatented). Breeder's code of new plant is 'D0209-3.'

The new *Osteospermum* was discovered and selected as a single flowering plant within the progeny of the stated population grown in Enkhuizen, Netherlands, in 1999. The new *Osteospermum* plant has been repeatedly asexually reproduced by cuttings in Enkhuizen, Netherlands over a period of 6 years. It has been found to retain its distinctive characteristics through successive propagations, and this novelty appears to be firmly fixed.

DESCRIPTION OF THE DRAWING

This new *Osteospermum* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Osteospermum* plant. The data which defines these characteristics were collected from asexual reproductions carried out in Enkhuizen, Netherlands. The plant history was taken on 25 weeks old plants. The instant plant was grown indoors in a 10.5 cm container and transplanted into the open field in week 20.

Color references are primarily to The R.H.S. Colour Chart of The Royal Horticultural Society of London, edition 2001.

TABLE 1

DIFFERENCES BETWEEN THE NEW CULTIVAR 'OSJASECLIPUR' AND TWO SIMILAR CULTIVARS

| | 'Osjaseclipur' | 'Osdapur' U.S. Plant Patent application Ser. No. 11/435,331 | 'Nasinga Purple' |
|---|---|---|---|
| Plant height | 24-26 cm | 20-24 cm | 40-45 cm |
| Plant width | 35-40 cm | 30-38 cm | 66-70 cm |
| Flower shape | Spatulate | Spatulate | Spatulate |
| Flowering response | Early | Early | Late |
| Flower size | 5-5.5 cm | 6 cm | 5.5 cm |
| Flower color | Light Purple | Dark Purple | Light Purple |

The Plant:
*Classification.*—Botanical: *Osteospermum ecklonis.*
Parentage:
*Female parent.*—Proprietary seedling selection 'C0254-3.'
*Male parent.*—Female is open pollinated so male is unknown.
Plant description:
*Growth habit.*—Round, wide.
*Plant height.*—24–26 cm.
*Speading area of plant.*—35–40 cm.
*Strength.*—Moderate growth.
*Branching character.*—Freely branching, 18 lateral branches without pinching.
*Blooming period.*—From May until October.
The stem:
*Length.*—20 cm.
*Diameter.*—2–3 mm.
*Internode length.*—15 mm.
*Texture.*—Glabrous.
*Color.*—RHS 144B.

The foliage:

*Shape.*—Single leaves, alternate and elliptic, apex: broadly acute. Base: attenuate, margin; irregular serration.

*Number of leaves per lateral branch.*—50.

*Texture.*—Glabrous, leathery, soft haris.

*Leaf.*—Color — Upper side: RHS 137B. Color — Under side: RHS 137C. Length: Young 20–25 mm, mature 40–45 mm. Width: Young 6 mm, mature 14–17 mm.

*Petiole.*—Absent.

The inflorescence:

*Number of inflorescences per mature plant.*—85.

*Inflorescence bud.*—Form: Ovoid. Length: 12–15 mm. Width: 7–9 mm. Color: RHS 79D.

*Inflorescence lastingness on the plant.*—Around 5 days depending on the temperature.

*Inflorescence.*—Diameter: 50–55 mm. Disc diameter: 10 mm.

*Inflorescence depth.*—13 mm.

*Fragrance.*—No frangrance.

*Disc florets.*—Shape: Tubular, elongated. Apex: Five pointed. Length: 6 mm. Width: 1 mm. Number of disc florets per inflorescence: 55. Color: RHS 92A.

*Ray florets.*—Length: 23–26 mm. Width: Apex 4 cm, middle 2 cm, base 4 cm. Shape: Capitulum with one series of ray florets; spatulate. Color — Upper surface: RHS 72D. Middle surface: RHS 84C. Lower surface: RHS N77B. Number of ray florets: 18–20. Shape Apex: Rounded. Base: Acute. Margin: Entire. Texture: Satiny.

*Peduncles.*—Length: 5–6.5 cm. Texture: Sturdy, tiny hairs. Color: RHS 148A. Diameter: 2 mm. Shape: Round.

*Phyllaries.*—Texture: Rough, tiny hairs. Number of phyllaries: 20. Color: RHS 144B. Length: 10 mm. Margin: Entire. Width: 1.5 mm. Apex: Acute. Shape: Ligulate. Color: RHS 137C both sides.

Reproductive organs:

*Androecium.*—Appearance: Present on disc florets only. Shape: Oblong, five stamens fused to one. Length: 2 mm. Width: 1 mm. Pollen color: RHS 24B. Total no. of anthers: 50.

*Gynoecium.*—Appearance: Present on both ray and disc florets. Pistil number: One pistil per ray or disc floret. Pistil length: 4 mm. Stigma color: RHS 77A. Stigma shape: Bipartite.

Seed development: Seed development has been observed on plants of the new *Osteospermum.*

*Amount of seeds produced.*—Moderate.

*Seed length.*—6 mm.

*Diameter.*—3 mm.

*Color.*—RHS 200A.

*Shape.*—Elliptic.

Disease resistance: Under commercial conditions, plants of the new *Osteospermum* are resistant to fungal pathogens common to *Osteospermum.*

What is claimed is:

1. A new and distinct variety of *Osteospermum* plant, substantially as illustrated and described herein.

* * * * *

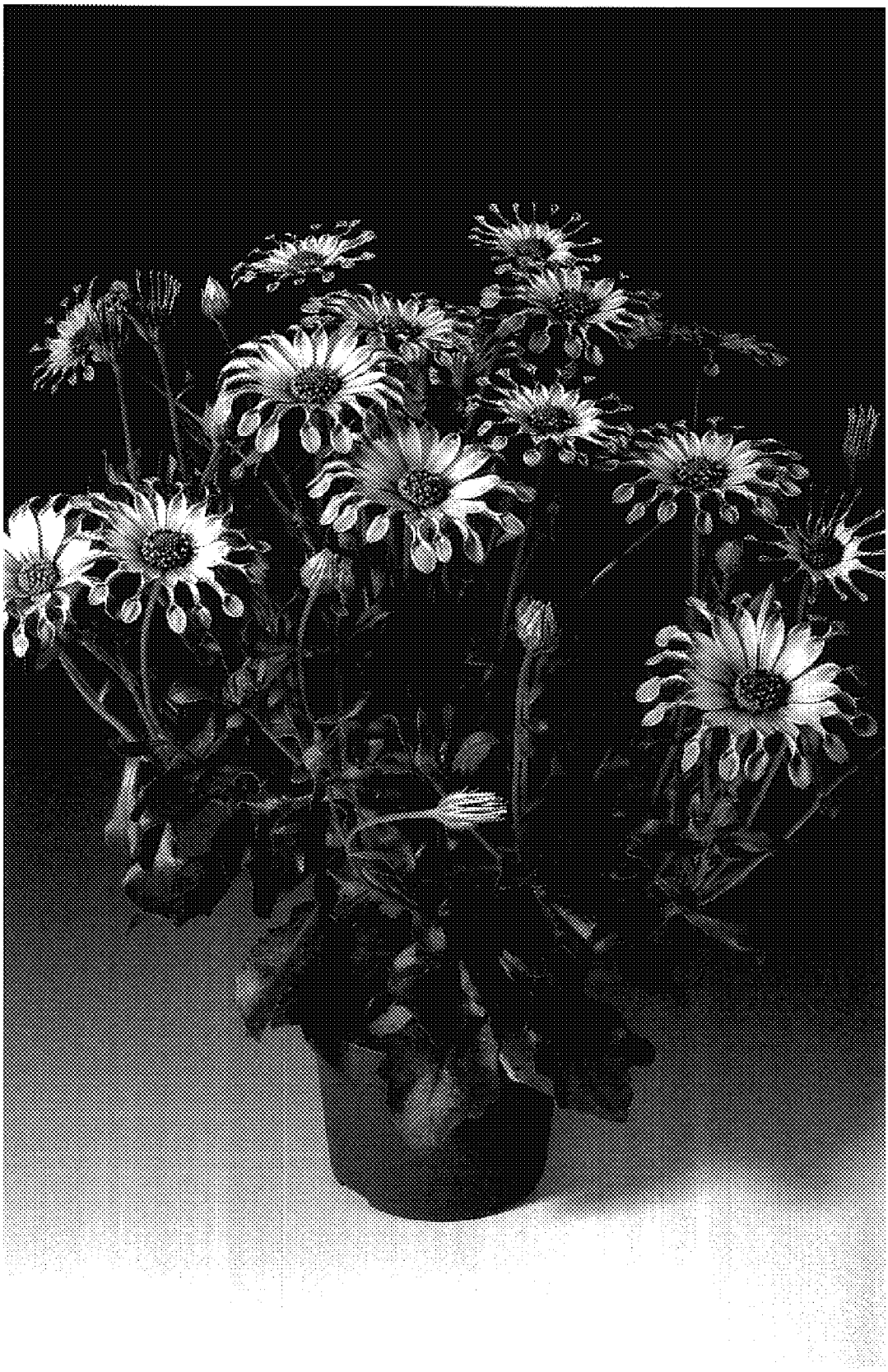

UNITED STATES PATENT AND TRADEMARK OFFICE

CERTIFICATE OF CORRECTION

PATENT NO. : PP 18,189 P2
APPLICATION NO. : 11/430147
DATED : November 6, 2007
INVENTOR(S) : Anna M.W.P. Houbraken It is certified that error appears in the above-identified patent and that said Letters Patent is hereby corrected as shown below:

At column 3, after "Texture" line 6, under "The foliage:", please delete "haris" and insert therefor --hairs--

At column 3, after "Fragrance" under "The inflorescence:", please delete "frangrance" and insert therefor --fragrance--

Signed and Sealed this

Twenty-sixth Day of February, 2008

JON W. DUDAS
*Director of the United States Patent and Trademark Office*